United States Patent
West et al.

(10) Patent No.: US 11,497,847 B1
(45) Date of Patent: Nov. 15, 2022

(54) WEARABLE INJECTOR WITH ADHESIVE SUBSTRATE

(71) Applicant: Fresenius Kabi Deutschland GmbH, Bad Homburg (DE)

(72) Inventors: Sharon D. West, Elkins Park, PA (US); Vladlena Belozerova, Philadelphia, PA (US)

(73) Assignee: Fresenius Kabi Deutschland GmbH, Bad Homburg (DE)

(*) Notice: Subject to any disclaimer, the term of this patent is extended or adjusted under 35 U.S.C. 154(b) by 0 days.

(21) Appl. No.: 17/180,494

(22) Filed: Feb. 19, 2021

(51) Int. Cl.
*A61M 5/142* (2006.01)

(52) U.S. Cl.
CPC . *A61M 5/14248* (2013.01); *A61M 2202/0007* (2013.01); *A61M 2205/02* (2013.01); *A61M 2209/088* (2013.01)

(58) Field of Classification Search
CPC .... A61M 5/14248; A61M 2005/14268; A61M 5/14244; A61M 2202/0007; A61M 2205/02; A61M 2209/088; A61B 5/257; A61B 5/6832; A61B 5/6833; A61B 5/688; A61B 8/4236; A61B 2050/002; A61K 9/703; A61K 9/7038; A61K 9/7084; A61K 51/1279
See application file for complete search history.

(56) References Cited

U.S. PATENT DOCUMENTS

| | | |
|---|---|---|
| 4,072,149 A | 2/1978 | Tischlinger |
| 4,234,104 A | 11/1980 | Apuzzo, Jr. et al. |
| 4,970,502 A | 11/1990 | Kunikane et al. |
| 6,620,134 B1 | 9/2003 | Trombley, III et al. |
| 8,285,328 B2 | 10/2012 | Caffey et al. |
| 9,452,255 B2 | 9/2016 | Tieck et al. |
| 2002/0169439 A1 | 11/2002 | Flaherty |
| 2003/0088238 A1 | 5/2003 | Poulsen et al. |
| 2003/0167036 A1 | 9/2003 | Flaherty |
| 2004/0068230 A1 | 4/2004 | Estes et al. |
| 2004/0116866 A1* | 6/2004 | Gorman ............ A61M 5/14248 604/93.01 |
| 2004/0199123 A1* | 10/2004 | Nielsen .................... A61M 5/14 424/449 |
| 2006/0111671 A1 | 5/2006 | Klippenstein |
| 2007/0290012 A1 | 12/2007 | Jackman |
| 2008/0091139 A1 | 4/2008 | Srinivasan et al. |

(Continued)

FOREIGN PATENT DOCUMENTS

| | | |
|---|---|---|
| EP | 2242034 A1 | 10/2010 |
| WO | 2018081234 A1 | 5/2018 |

(Continued)

OTHER PUBLICATIONS

RightCare CGM Adhesive Universal Overpatches; Amazon available for sale May 6, 2020. https://www.amazon.com/Adhesive-Universal-Covered-Synthetic-Extreme/dp/B083QMYXQ7/ref=sr_1_27?keywords=overpatch&qid=163080153&sr=8-27&th=1 (Year: 2020).

(Continued)

*Primary Examiner* — Jason E Flick
(74) *Attorney, Agent, or Firm* — Cook Alex Ltd.

(57) ABSTRACT

An on-body drug delivery device having a housing carried by a substrate. The substrate includes one or more cut-outs and/or one or more perforations to allow the substrate to better conform to the patient's body.

19 Claims, 4 Drawing Sheets

(56) References Cited

U.S. PATENT DOCUMENTS

| | | |
|---|---|---|
| 2009/0131860 A1* | 5/2009 | Nielsen ............. A61M 5/14248 604/66 |
| 2010/0130931 A1 | 5/2010 | Yodfat et al. |
| 2011/0178461 A1 | 7/2011 | Chong et al. |
| 2011/0196304 A1 | 8/2011 | Kramer et al. |
| 2012/0010594 A1 | 1/2012 | Holt et al. |
| 2013/0006213 A1 | 1/2013 | Arnitz et al. |
| 2015/0374919 A1 | 12/2015 | Gibson |
| 2016/0020798 A1 | 1/2016 | Chen |
| 2016/0038689 A1* | 2/2016 | Lee .................. A61M 5/19 604/113 |
| 2016/0082182 A1 | 3/2016 | Gregory et al. |
| 2016/0175515 A1 | 6/2016 | McCullough |
| 2016/0199574 A1 | 7/2016 | Ring et al. |
| 2016/0220798 A1 | 8/2016 | Netzel et al. |
| 2016/0296704 A1 | 10/2016 | Gibson |
| 2016/0354555 A1 | 12/2016 | Gibson et al. |
| 2016/0374707 A1 | 12/2016 | Akagane |
| 2017/0119969 A1 | 5/2017 | McCullough et al. |
| 2017/0124284 A1 | 5/2017 | McCullough et al. |
| 2017/0147787 A1 | 5/2017 | Albrecht et al. |
| 2017/0182253 A1 | 6/2017 | Folk et al. |
| 2017/0312454 A1 | 11/2017 | Chattaraj et al. |
| 2017/0340837 A1 | 11/2017 | Nazzaro et al. |
| 2017/0361015 A1 | 12/2017 | McCullough |
| 2017/0368260 A1 | 12/2017 | McCullough et al. |
| 2018/0021508 A1 | 1/2018 | Destefano et al. |
| 2018/0028747 A1 | 2/2018 | Hanson et al. |
| 2018/0036476 A1 | 2/2018 | McCullough et al. |
| 2018/0085517 A1 | 3/2018 | Laurence et al. |
| 2018/0193557 A1 | 7/2018 | Johnson et al. |
| 2018/0256823 A1 | 9/2018 | Nazzaro et al. |
| 2018/0272059 A1 | 9/2018 | Marbet et al. |
| 2018/0304014 A1 | 10/2018 | Knudsen et al. |
| 2019/0009019 A1 | 1/2019 | Shor et al. |
| 2019/0022306 A1 | 1/2019 | Gibson et al. |
| 2019/0050375 A1 | 2/2019 | Fitzgibbon et al. |
| 2019/0060562 A1 | 2/2019 | Olivas et al. |
| 2019/0083702 A1 | 3/2019 | Nekouzadeh et al. |
| 2019/0134296 A1 | 5/2019 | Barbedette et al. |
| 2019/0143043 A1 | 5/2019 | Coles et al. |
| 2019/0143047 A1 | 5/2019 | Jazayeri et al. |
| 2019/0151544 A1 | 5/2019 | Stonecipher |
| 2019/0167899 A1 | 6/2019 | Cabiri |
| 2019/0167908 A1 | 6/2019 | Fitzgibbon et al. |
| 2019/0192766 A1 | 6/2019 | Stonecipher |
| 2019/0247579 A1 | 8/2019 | Damestani |
| 2019/0275241 A1 | 9/2019 | Ring et al. |
| 2019/0328965 A1 | 10/2019 | Moberg |
| 2019/0365986 A1 | 12/2019 | Coiner et al. |
| 2019/0374707 A1 | 12/2019 | Damestani et al. |
| 2019/0381238 A1 | 12/2019 | Stonecipher et al. |
| 2020/0023122 A1 | 1/2020 | McCullough et al. |
| 2020/0164145 A1 | 5/2020 | Chang et al. |
| 2020/0164155 A1 | 5/2020 | Mojarrad et al. |
| 2020/0179609 A1 | 6/2020 | Tan-Malecki et al. |
| 2020/0197628 A1 | 6/2020 | McCullough et al. |
| 2020/0206429 A1 | 7/2020 | Hering et al. |
| 2020/0230313 A1 | 7/2020 | Mojarrad et al. |
| 2020/0238004 A1 | 7/2020 | McCullough |
| 2020/0254172 A1 | 8/2020 | Forster et al. |
| 2020/0254185 A1 | 8/2020 | Bar-el et al. |
| 2020/0261643 A1* | 8/2020 | Boyaval ............ A61M 5/14248 |
| 2020/0261648 A1 | 8/2020 | Groszmann et al. |
| 2020/0261657 A1 | 8/2020 | Gibson et al. |
| 2020/0289745 A1 | 9/2020 | Harris et al. |
| 2020/0297927 A1 | 9/2020 | Conrath et al. |
| 2020/0315918 A1 | 10/2020 | Naygauz |
| 2020/0322793 A1 | 10/2020 | Yang |
| 2020/0338271 A1 | 10/2020 | Harris et al. |
| 2021/0228799 A1 | 7/2021 | Streit et al. |

FOREIGN PATENT DOCUMENTS

| | | |
|---|---|---|
| WO | 2018183039 A1 | 10/2018 |
| WO | 2018226565 A1 | 12/2018 |
| WO | 2019018169 A1 | 1/2019 |
| WO | 2019022950 A1 | 1/2019 |
| WO | 2019022951 A1 | 1/2019 |
| WO | 2019032101 A1 | 2/2019 |
| WO | 2019143753 A1 | 7/2019 |

OTHER PUBLICATIONS

Omnipod Grip Shield Designed by Deck My Diabetes; Amazon. Available for sale Dec. 14, 2020 https://www.amazon.com/Deck-My-Diabetes-Flexible-Additional/dp/B08QL3TVZB/ref=sr_1_6?keywords=insulin+pump+overlay&qid=1639074568&sr=8-6 (Year: 2020).

* cited by examiner

WEARABLE INJECTOR WITH ADHESIVE SUBSTRATE

FIELD OF THE DISCLOSURE

The present disclosure relates to drug delivery/infusion devices. More particularly, the present disclosure relates to devices mounted to the body for automatically delivering a drug to a patient. Even more particularly, the present disclosure relates devices mounted to the body of a patient, the device including a substrate securely adhered and conformed to the body of the patient such that the risk of dislodgement of the device is minimized.

DESCRIPTION OF RELATED ART

Delivery of liquid drugs to a patient via injection using a needle or syringe is well-known. More recently, devices that automate the delivery of liquid drugs have been introduced. These devices (which are commonly referred to as "on-body devices" or "on-body injectors") are mounted or otherwise secured to the body of the patient (e.g., to the arm or abdomen) and remain in place for an extended amount of time (on the order of hours or days), injecting an amount of the drug into the body of the patient at one or more scheduled times. For example, a device may be configured to deliver a drug over the span of 45 minutes, with delivery beginning 27 hours after the device has been activated and applied to a patient (to ensure that the drug is not delivered sooner than 24 hours after a medical procedure or treatment). These devices improve upon manual methods by obviating the need for the patient to inject themselves with the drug (which carries heightened risks of the patient improperly administering the injection or injecting the drug at an inappropriate time) or to return to a medical facility for one or more injections by a technician or medical professional.

Figure 1:
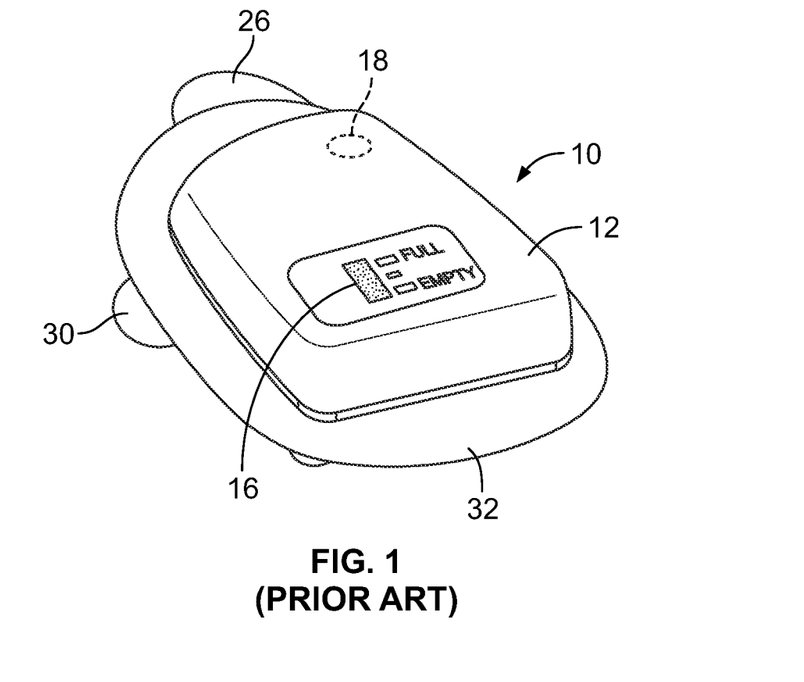
FIG. 1 is a top perspective view of a drug delivery device according to conventional design.
Figure 2:
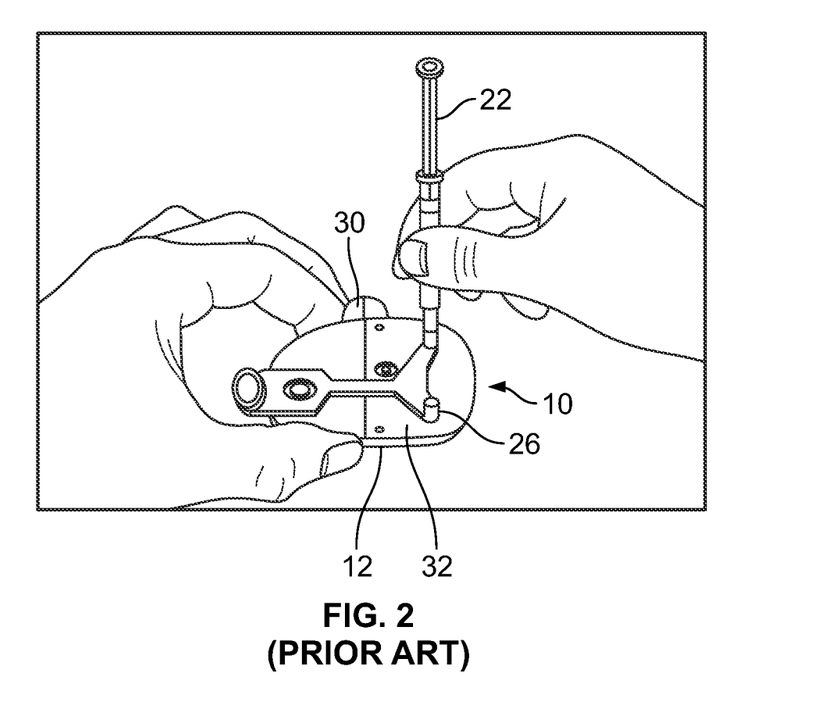
FIG. 2 is a bottom perspective view of the drug delivery device of FIG. 1.
Figure 3:
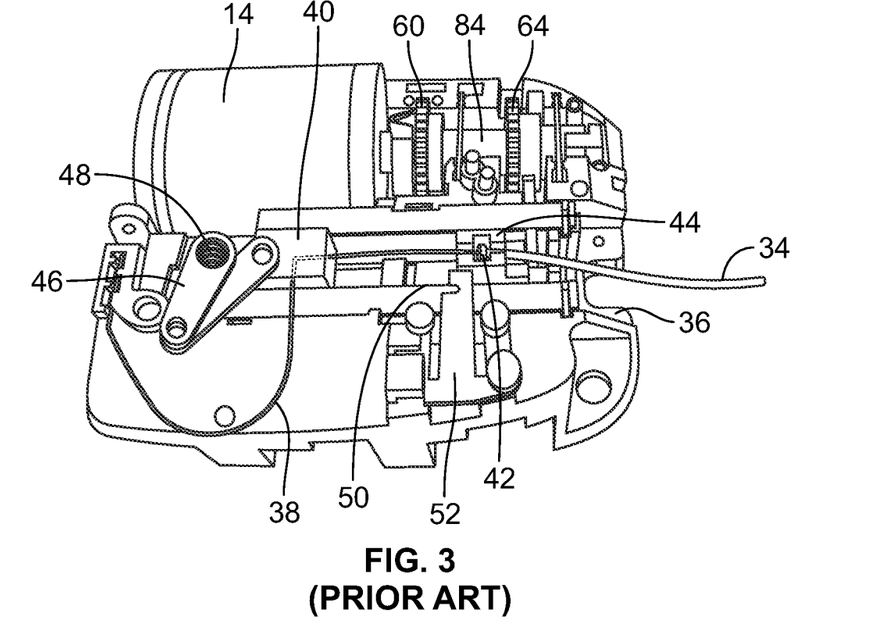
FIG. 3 is a top perspective view of the interior components of the drug delivery device of FIG. 1.
Figure 4:
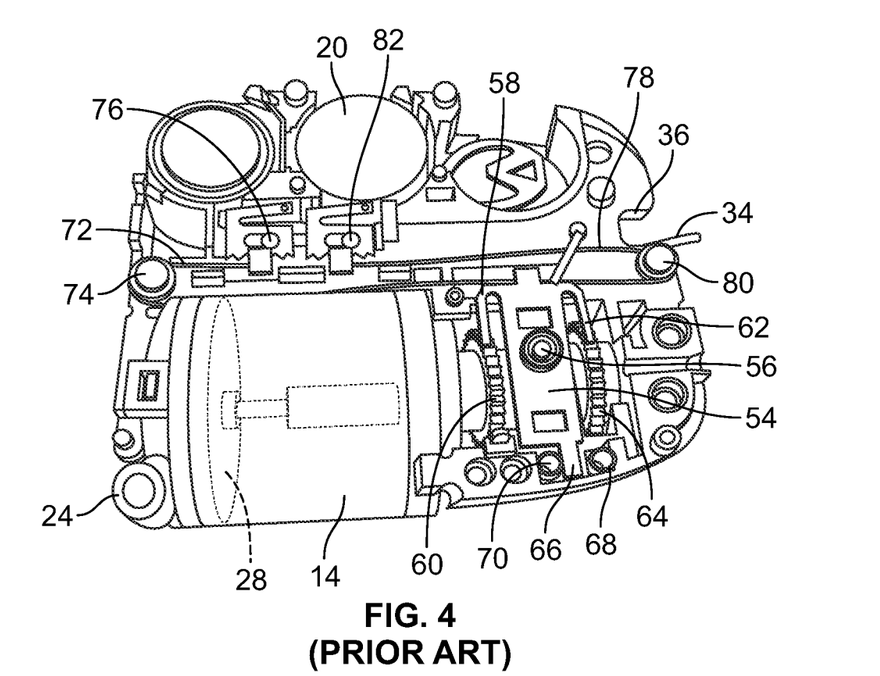
FIG. 4 is a bottom perspective view of the interior components of the drug delivery device of FIG. 1.

One known on-body device 10 is shown in FIGS. 1 and 2. The device 10 of FIG. 1 includes a housing 12 that contains or encloses the functional components of the device 10, which are shown in FIGS. 3 and 4.

The internal components of the device 10 include a reservoir 14 that is configured to be filled with a liquid drug to be delivered to the patient. An upper surface of the housing 12 includes a fill indicator 16 that provides a visual indication of the amount of fluid in the reservoir 14. In addition to the fill indicator 16, the upper surface of the housing 12 may include printed information, such as information regarding the drug to be delivered. The upper surface of the housing 12 may be formed of a translucent material, which allows light from a status light 18 (which may be configured as a light-emitting diode) mounted within the housing 12 (FIG. 1) to be seen through the upper surface of the housing 12. The status light 18 is electrically coupled to a controller or processor (which may be a CPU or MPU configured as a computer chip mounted to a printed circuit board positioned within the housing 12, for example) that carries software for executing a drug delivery routine. The status light 18 receives signals from the controller and emits light to provide information regarding a status of the device 10. This may include emitting differently colored light and/or emitting light in different flashing patterns to indicate different conditions, such as a blinking orange light to indicate that the device 10 is ready to be applied to a patient, a blinking green light to indicate proper operation of the device 10, and a blinking red light to indicate an error or other condition. One or more batteries 20 provide power to the status light 18 and the other electrical components of the device 10.

The drug is injected into the reservoir 14 using a (typically pre-filled) syringe 22 via a port 24 incorporated into the bottom or underside of the housing 12 (FIG. 4) and fluidically connected to the reservoir 14. FIGS. 1 and 2 illustrate an applicator 26 that is removably associated with the underside of the housing 12 and used in combination with the syringe 22 to fill the reservoir 14 via the port 24. The drug is most typically injected into the reservoir 14 by a medical professional immediately before the device 10 is secured to the patient to ensure that the proper drug is supplied, along with the proper amount.

A piston or plunger 28 (FIG. 4) positioned within the reservoir 14 is moved (from left to right, in the orientation of FIG. 4) as the space within the reservoir 14 is filled by the inflowing drug. Movement of the piston 28 into its final position (when the reservoir 14 has been filled with the appropriate amount of the drug) causes a portion of a rod associated with the piston 28 to extend from the reservoir 14 to create an electrical connection, which activates the device 10. Activation of the device 10 may include a signal, such as a buzzer providing an audible indication that the device 10 has been activated and/or a light emitted by the status light 18.

When the device 10 has been activated, it is mounted or secured to the body of the patient. The applicator 26 is first removed from the underside of the housing 12 and discarded, followed by a pull tab 30 being manipulated to remove a release film from an adhesive pad 32 (substrate) associated with the underside of the housing 12. The housing 12 is then pressed against the body of the patient, with the adhesive pad 32 (adhesive side of the substrate) facing the body. An adhesive present on the adhesive pad/substrate 32 causes the adhesive pad 32 (and, hence, the housing 12) to adhere to the body. Examples of devices using adhesive pads/substrates are described in U.S. Patent Application Publication 2019/0083702 and International Patent Application Publication WO2018/081234, the contents of which are incorporated by reference herein in their entireties.

Some predetermined time after the device 10 has been activated (which may be on the order of three to five minutes, for example), a distal end portion of a cannula 34 is introduced into the skin of the patient via a cannula window 36 defined in the housing 12 (FIGS. 3 and 4). The cannula 34 (which remains partially positioned within the skin of the patient for as long as the device 10 is in use) is formed of a flexible or semi-rigid material, such as a plastic material, for improved patient comfort.

As the cannula 34 is not itself configured to pierce the skin, an associated needle 38 is provided within the lumen of the cannula 34, with a sharp or beveled distal end of the needle 38 extending out of a distal end of the cannula 34. A midsection of the needle 38 is mounted within a needle carriage 40, while a proximal end 42 of the cannula 34 is mounted within a cannula carriage 44 that is initially positioned directly adjacent to the needle carriage 40. The needle carriage 40 is pivotally connected to an end of a linkage or crank arm 46, with an opposite end of the linkage 46 being associated with a torsion spring 48. At the designated time (e.g., 3-5 minutes after the device 10 has been activated), the controller causes a lever (not visible) to be released, which allows the spring 48 to recoil, in turn rotating the linkage 46, which rotation causes the needle carriage 40 to move along a linear track 50 from a first position adjacent to the spring 48 (FIG. 3) to a second position spaced away from the spring 48. Movement of the needle carriage 40 causes corresponding movement of the cannula carriage 44 along the track 50, with the cannula 34 and the distal portion of the needle 38 moving together in a direction away from the spring 48. Moving the carriages 40 and 44 into the second position causes the sharp distal end of the needle 38 to advance out of the housing 12 via the cannula window 36 and pierce the skin. The cannula 34 is carried by or moves along with the distal portion of the needle 38, such that the needle 38 piercing the skin will also cause the distal end of the cannula 34 to enter into the skin.

Continued recoiling of the spring 48 causes further rotation of the linkage 46, which has the effect of moving the needle carriage 40 back toward the spring 48 (i.e., back toward its first position). Rather than moving along with the needle carriage 40, the cannula carriage 44 is held in its second position (FIG. 3) by a lock or latch 52. As the movement of the needle carriage 40 is not restricted by the lock or latch 52, the needle carriage 40 will return to its first position, while the cannula carriage 44 remains in its second position (with the final positions of both carriages 40 and 44 shown in FIG. 3).

Movement of the needle carriage 40 in a proximal direction away from the cannula carriage 44 causes the needle 38 to partially (but not fully) retract from the cannula 34. In the final condition shown in FIG. 3, the distal end of the needle 38 is positioned within the cannula 34 (e.g., adjacent to a midsection or midpoint of the cannula 34), while the distal end of the cannula 34 remains positioned within the skin. A proximal end of the needle 38 extends into fluid communication with the reservoir 14, such that the needle 38 provides a fluid path from the reservoir 14 to the cannula 34 when the carriages 40 and 44 are in the final condition illustrated in FIG. 3. Due to the distal end of the cannula 34 remaining positioned within the skin, subsequent advancement of the drug out of the reservoir 14 (e.g., 27 hours after the device 10 has been activated) will cause the drug to move into the needle 38 (via the proximal end of the needle 38), through the needle 38 (to its distal end), and into the cannula 34. The drug is then delivered to the patient (e.g., over the course of a 45-minute session) via the distal end of the cannula 34 positioned within the skin.

As for the mechanism by which the drug is advanced out of the reservoir 14, the device 10 includes a lever 54 mounted to a pivot point 56 (FIG. 4). The lever 54 includes a first arm 58 configured and oriented to interact with a first gear 60 and a second arm 62 configured and oriented to interact with a second gear 64. A tab 66 extends from an opposite end of the lever 54 and is configured and oriented to alternately move into and out of contact with two electrical contacts 68 and 70 (electrically coupled to a printed circuit board, which is not shown) as the lever 54 pivots about the pivot point 56.

A first wire or filament 72 extends from the lever 54, around a first pulley 74, and into association with a first electrical contact 76. A second wire or filament 78 extends from the lever 54 in the opposite direction of the first wire 72, around a second pulley 80, and into association with a second electrical contact 82. The wires 72 and 78 (which are commonly referred to as "muscle wires") are formed of a shape memory alloy (e.g., Nitinol), which causes them to heat up and contract when a current flows through them, while being allowed to stretch when the current is removed and the wire 72, 78 cools. Current is alternately applied to the two wires 72 and 78, causing the one carrying a current to heat up and contract while the other one is allowed to stretch. The wire 72, 78 that contacts will pull on the lever 54, causing it to pivot about the pivot point 56. Thus, alternately applying current to the two wires 72 and 78 will cause the wires 72 and 78 to alternately contact and stretch, which in turn causes the lever 54 to pivot back and forth about the pivot point 56.

At the designated time (e.g., 27 hours after the device 10 has been activated), the controller provides commands that cause current to be alternately applied to the muscle wires 72 and 78, which causes the lever 54 to alternately pivot about the pivot point 56 in opposite first and second directions. Pivotal movement of the lever 54 in the first direction will cause the first arm 58 of the lever 54 to engage and rotate the first gear 60 an incremental amount, while pivotal movement of the lever 54 in the second direction will cause the second arm 62 of the lever 54 to engage and rotate the second gear 64 an incremental amount (in the same direction in which the first gear 60 is rotated by the first arm 58). Both gears 60 and 64 are associated with a common shaft 84 (which is shown in FIG. 3 and may be formed with gears 60 and 64 as a singled, molded piece), such that rotation of either gear 60, 64 will cause the shaft 84 to rotate about its central axis. The shaft 84 is mechanically coupled to the piston 28 within the reservoir 14, with rotation of the shaft 84 causing the piston 28 to move toward its initial position (e.g., by a threaded connection whereby rotation of the shaft 84 is translated into movement of the piston 28 along the length of the reservoir 14). As the piston 28 moves toward its initial position (from right to left in the orientation of FIG. 4), it will force the drug out of the reservoir 14 via the proximal end of the needle 38. As described above, the drug will flow through the needle 38, into and through the cannula 34, and into the body of the patient.

After the drug has been delivered (e.g., over the course of a 45-minute session), the controller alerts the patient via a visual cue from the status light 18 and/or an audible cue from the buzzer that drug delivery is complete. Subsequently, the patient removes the device 10 from their skin and discards the device 10.

While devices of the type described above have proven adequate, there is room for improvement. For example, it would be desirable that the substrate that carries the device and allows the device to be mounted on the skin of a patient remains reliably affixed to the patient's skin and does not become dislodged or allow for leaks from the device. In that regard, it would be desirable that the substrate conform to the curved surface of the body and stretch and deform, as necessary, during normal body movements of the wearer. It would also be desirable to be able to adjust the size of the substrate to the particular patient. In that regard, it would be desirable to provide an on-body drug-delivery device that includes a substrate of the type described herein that may also be adjustable in size.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In a first aspect, an on-body drug delivery device includes a housing having a cover and a bottom wall. The device includes a substrate that comprises a sheet of flexible material having a top surface and a bottom surface. The housing is carried by the substrate, the sheet including one or more cut-outs and/or one or more perforations in the sheet.

In a more particular aspect, the substrate has a top surface and a bottom surface. The bottom surface may include a layer of adhesive.

In another more particular aspect, the on-body drug delivery device includes a substrate including both cut-outs and perforations. In another more particular aspect, the substrate includes only cut-outs or only perforations.

In accordance with another aspect, the substrate includes an outer edge defining a perimeter around the housing. The one or more cut-outs and/or one or more perforations are on the perimeter of the substrate.

BRIEF DESCRIPTION OF THE DRAWINGS

FIG. 7b is an enlarged schematic depiction of cut-outs in the adhesive substrate of the drug delivery device of FIG. 7a.

DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific designs and features disclosed herein are not to be interpreted as limiting the subject matter as defined in the accompanying claims.

In keeping with the present disclosure, and with reference to FIGS. 5-8, the drug delivery/infusion device 10 (which may have a modular construction) comprises a main body or housing 90 that houses many of the electro-mechanical components of the device and a removable cartridge that is pre-filled and/or refillable with a drug. A removable cartridge (not shown) permits re-filling and reuse of the infuser without having to remove it from the patient after the initial attachment and permits the device to be used to deliver more than one type of drug. A separable pre-filled cartridge also facilitates storage of the drug (which would be refrigerated) apart from the main body/housing 90, which may be stored at room temperature, thus reducing the amount of refrigerated storage space required. The cartridge further comprises a pre-filled drug chamber, a piston/plunger, and a structure for pressurizing the drug held within the chamber for delivery to the patient. While a removable cartridge may be advantageous, it is also within the scope of the present disclosure for the device to be provided as a single-use item, with a pre-filled or fillable drug chamber or reservoir, as in conventional devices.

Figure 5:
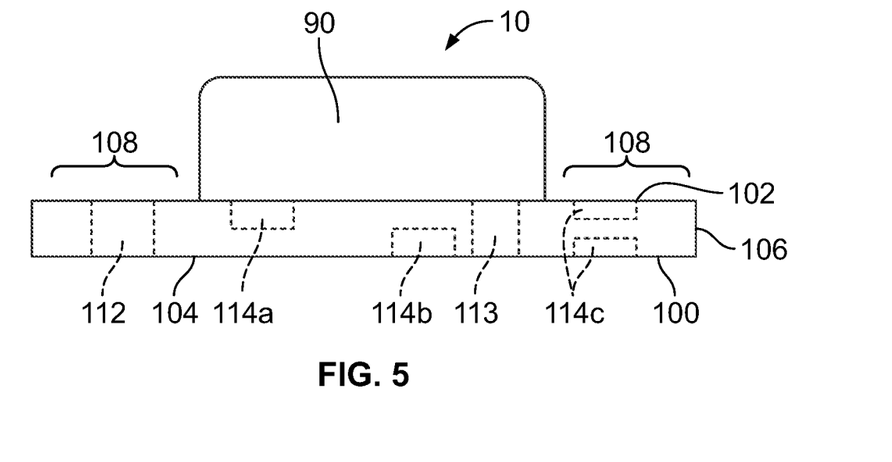
FIG. 5 is a schematic side view of a drug delivery/infusion device according to the present disclosure.
Figure 6:
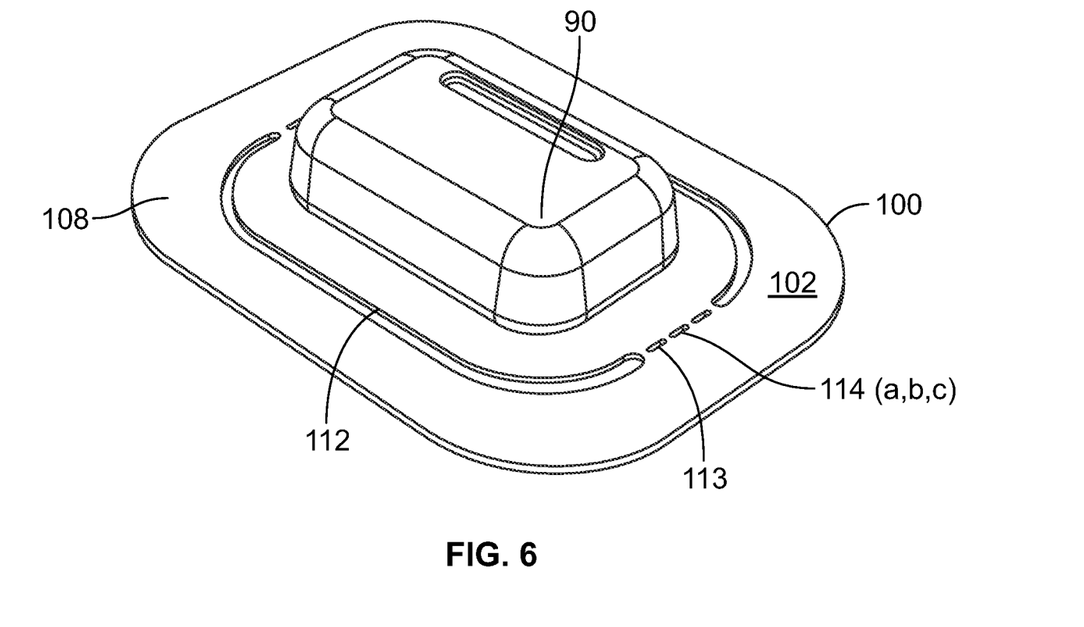
FIG. 6 is a perspective view of a drug delivery device with a first embodiment of an adhesive substrate.
Figure 7A:
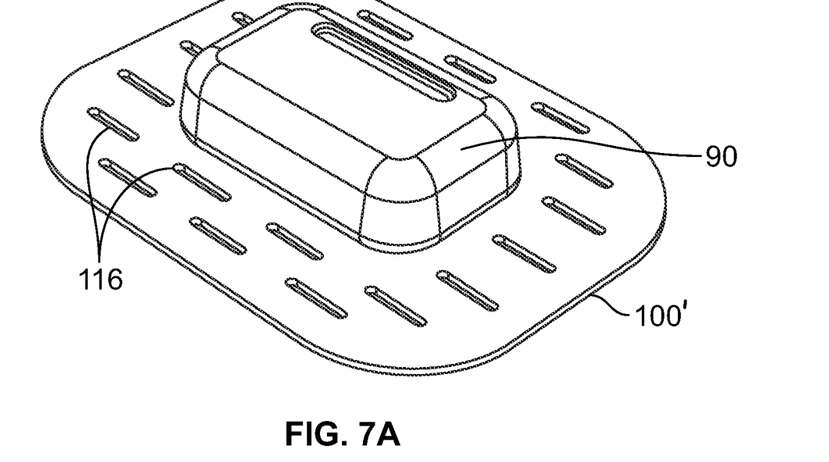
FIG. 7a is a perspective view of a drug delivery device with another embodiment of an adhesive substrate.
Figure 7B:
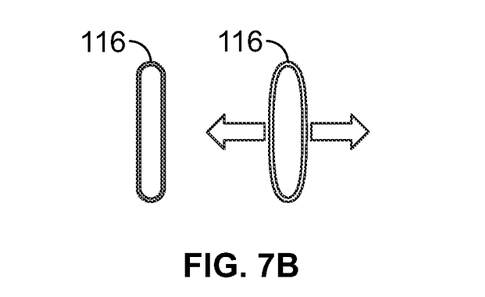
Figure 8:
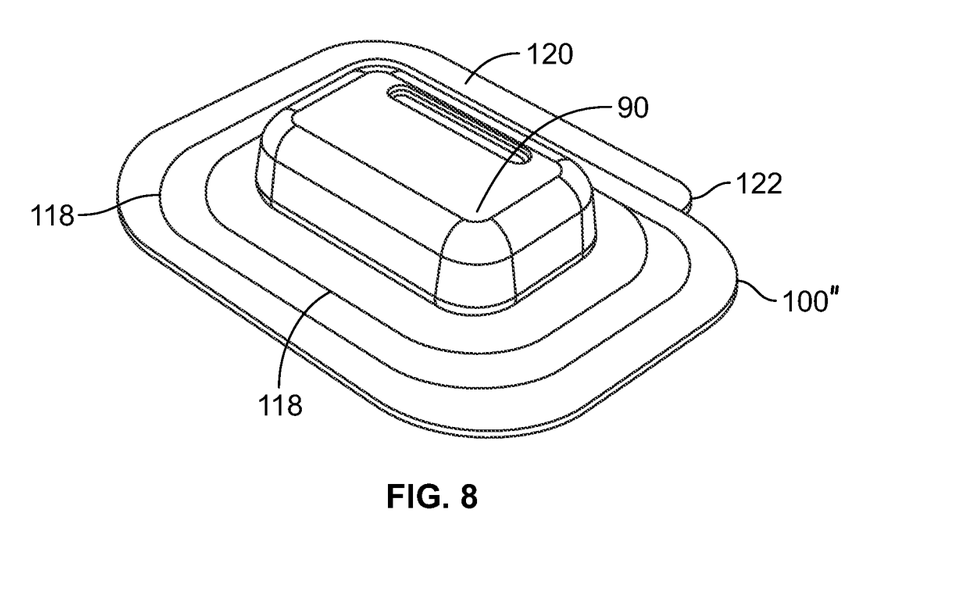
FIG. 8 is a perspective view of a drug delivery device with a further embodiment of an adhesive substrate.

Housing 90 is affixed to and carried by a substrate 100 which may be affixed or adhered to the patient's body. As shown in FIG. 5, substrate 100 may take the form of a flat sheet or pad having a top surface 102 and a bottom surface 104 and further defined by a peripheral edge 106. Substrate may have a rectangular shape with rounded corners, as shown in FIGS. 6-8, or any other suitable shape and size that can accommodate housing 90. In this regard, it may be preferable that substrate 100 include a dimension, such as surface area, that is greater than the surface area of bottom wall of housing 90, thereby defining a perimeter 108 between the outside edge of housing 90 and peripheral edge 106 of substrate 100.

Substrate 100 is preferably made of a flexible, resilient material that can be stretched (as will be described in greater detail below.) Substrate 100 may further include upper and lower bacteria impermeable liners as described in US Patent Application Publication US 2019/0083702, the contents of which are incorporated herein by reference. The exposed surface of peripheral edge may likewise include and be covered by a bacterial impermeable liner.

The flexible, resilient material of substrate 100 may be any such material that can be safely applied and adhered to the skin of the patient. Typically, substrate 100 is made of non-woven, fibrous material. Examples of suitable materials include polyethylene, polyvinyl chloride, polyurethane, polyethylene terephthalate, polypropylene, viscose/rayon, thermoplastic elastomer and the like.

As discussed above, infusion device is to be worn by the patient and must be removably affixed or adhered to the skin of the patient. In one embodiment, substrate 100 may include or be otherwise provided with an adhesive on bottom surface 104. The adhesive is such that the substrate remains adhered to the patient's body and cannot be easily dislodged or separated from the patient's skin. In that regard, the adhesive should be waterproof and/or resistant to degradation by perspiration. In addition, adhesive substrate should tightly conform to the skin of the patient to keep the needle of the device from dislodging. At the same time, the adhesive is not permanent and, when necessary, can be removed routinely by a medical professional in an "out-patient" procedure or even by the patient. Examples of suitable adhesives useful with the substrates include any medical-grade or skin contact adhesives such as, but not limited to, acrylic or acrylate compositions, synthetic rubber, hydrocolloid, silicone and the like.

Turning now to FIGS. 5 and 6, there is shown a drug delivery/infusion device 10 including housing 90 (which contains the injector and drug delivery components) carried by adhesive substrate 100. As discussed above, substrate includes a perimeter 108 defined by the outer edge of housing 90 and the peripheral edge 106 of substrate 100. As further shown, perimeter 108 may include one or more cut-outs 112, perforations 113, and/or partial perforations 114. As shown schematically in FIG. 5, cut-outs 112 are slots that extend through the entire thickness of substrate 100. Perforations 113 are similar to cut-outs 112 in that they extend through the entire thickness of substrate 100 but are typically shorter in length. Partial perforations 114 (also shown schematically in FIG. 5) are similar to perforations 113 (being relatively short in length) but, rather than being short slots extending through the entire thickness of the substrate 100, are areas of reduced thickness that do not extend all the way through the substrate 100. Thus, it will be understood that the term "perforation" may include a perforation 113 (a perforation that extends through the entire thickness of the substrate) or a partial perforation 114 (an area of reduced thickness that does not extend all the way through the surface). As best shown in FIG. 5, the partial perforations may be defined in the top surface of the substrate (shown as perforation 114a in FIG. 5) or in the bottom surface of the substrate (shown as perforation 114b in FIG. 5) or may comprise a first portion defined in the top surface and a second portion defined in the bottom surface and at least partially aligned with the first portion (shown as perforation 114c in FIG. 5).

In the embodiment of FIG. 6, substrate includes cut-outs within perimeter 108, partially surrounding housing 90 and interrupted by a plurality of perforations 113 and/or partial perforations 114. It will be understood that the substrate 100 may include only one or more cut-outs, or only one or more perforations or, as in FIG. 6, a combination of cut-outs and perforations in a pre-selected arrangement. If a substrate includes a plurality of partial perforations, all of the partial perforations may be defined in the same surface of the substrate (i.e., all defined in the top surface or all defined in the bottom surface) or at least two of the perforations may be defined in different surfaces of the substrate. Further, if at least two partial perforations are provided, they may have the same or different depths (i.e., reduce their associated portions of the substrate to different thicknesses).

An alternative embodiment of the drug delivery/infusion device 10 is shown in FIG. 7a. The embodiment of FIG. 7a includes a plurality of cut-outs or perforations or partial perforations 116 (e.g., of the type described above and shown in FIGS. 5 and 6) spaced across the perimeter 108 of substrate 100'. Cut-outs or perforations or partial perforations 116 allow substrate 100' to be stretched and deformed in the manner shown in FIG. 7b to adjust (expand) the size of the substrate and/or to better conform substrate 100' to the contours of the patient's body.

A further alternative of drug delivery/infusion device 10 is shown in FIG. 8. In the embodiment of FIG. 8, substrate 100" includes a continuous (or semi-continuous) perforation 118 (which may be a perforation that extends through the entire thickness of the substrate or a partial perforation) that spirals around housing 90, defining a continuous spiral strip 120. Beginning end 122 of strip 120 provides a pull tab for the user. Perforation(s) 118 provides a line along which adjacent strip portions can be separated or stretched to adjust the size of substrate 100". More particularly, portions of strip 120 can be separated from each other to reduce the size of substrate 100". For example, the outermost ring(s) of strip 120 may be peeled away from adjacent interior ring(s) of strip 120 and severed to reduce the overall area of the substrate to a desired size.

Adhesive substrates of the type described above improve the comfort level for the patient user and reduce the likelihood of dislodgement of the delivery device 10 by conforming and better securing the device to the patient's body. Providing cut-outs and/or perforations allows the substrate to better stretch and deform than a solid sheet and allow the adhesive substrate to be adjusted on a patient-by-patient basis. Moreover, cut-outs and perforations also allow the substrate to be expanded (by stretching) or reduced (by tearing) in size in accordance with the needs of the patient user.

The methods and devices described herein may be used to deliver any suitable fluid medication to a subject. In an exemplary embodiment, the methods and devices described herein are used to deliver pegfilgrastim to a subject, though other exemplary medications include (without limitation) one or more of the following: adalimumab, rituximab, risankizumab, etanercept, trastuzumab, ado-trastuzumab emtansine, trastuzumab deruxtecan, bevacizumab, infliximab, pegfilgrastim, filgrastim, tocilizumab, golimumab, interferon beta-1a, ranibizumab, denosumab, pembrolizumab, nivolumab, aflibercept, eculizumab, ocrelizumab, pertuzumab, secukinumab, omalizumab, ustekinumab, vedolizumab, daratumumab, dupilumab, atezolizumab, natalizumab, bortezomib, ipilimumab, durvalumab, emicizumab, palivizumab, guselkumab, mepolizumab, panitumumab, ramucirumab, belimumab, abatacept, certolizumab pegol, ixekizumab, romiplostim, benralizumab, evolocumab, canakinumab, obinutuzumab, cetuximab, erenumab, blinatumomab, romosozumab, mirikizumab, inotuzumab, sacituzumab govitecan, enfortumab vedotin, brentuximab vedotin.

It will be understood that the embodiments and examples described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. An on-body drug delivery device comprising:
a) a housing comprising a cover and a bottom wall and an outside edge; and
b) a substrate comprising a sheet of flexible material having a top surface and a bottom surface,
wherein said housing is carried by said substrate, said substrate comprising a continuous peripheral edge, said peripheral edge of said substrate and said outside edge of said housing defining a perimeter around said housing with a plurality of perforations defined within and around said perimeter, wherein the sheet has different reduced thicknesses at the locations of at least two of said plurality of perforations.

2. The on-body drug delivery device of claim 1 wherein said sheet includes a dimension that is larger than a dimension of said housing bottom wall.

3. The on-body drug delivery device of claim 1 wherein said bottom wall is adhered to said top surface of said substrate.

4. The on-body drug delivery device of claim 1 wherein said bottom surface of said substrate comprises a layer of adhesive.

5. The on-body drug delivery device of claim 1 wherein said flexible material comprises one of polyethylene, polyvinyl chloride, polyurethane, polyethylene terephthalate, polypropylene, viscose/rayon, and thermoplastic elastomer.

6. The on-body drug delivery device of claim 1 wherein said substrate comprises both cut-outs and perforations.

7. The on-body delivery device of claim 1 wherein said substrate comprises only perforations.

8. The on-body drug delivery device of claim 1 wherein said perimeter comprises a plurality of cut-outs surrounding said housing.

9. The on-body drug delivery device of claim 1 wherein said sheet comprises a continuous spiraling perforation within said perimeter defining a spiral strip about said housing.

10. The on-body drug delivery device of claim 9 wherein an end of said spiral strip defines a pull tab.

11. The on-body drug delivery device of claim 1 comprising discontinuous cut-outs in the substrate perimeter.

12. The on-body drug delivery device of claim 11 comprising one or more perforations between said discontinuous cut-outs.

13. The on-body drug delivery device of claim 4 wherein said adhesive is selected from the group consisting of acrylic or acrylate compositions, synthetic rubber, hydrocolloid, and silicone.

14. The on-body drug delivery device of claim 1 wherein at least one of said one or more perforations is defined in the top surface of the sheet.

15. The on-body drug delivery device of claim 1 wherein at least one of said one or more perforations is defined in the bottom surface of the sheet.

16. The on-body drug delivery device of claim 1 wherein at least one of said one or more perforations comprises a first portion defined in the top surface of the sheet and a second portion defined in the bottom surface of the sheet.

17. The on-body drug delivery device of claim 1 comprising a plurality of perforations, wherein at least one of said plurality of perforations is defined in the top surface of the sheet and at least one of said plurality perforations is defined in the bottom surface of the sheet.

18. The on-body drug delivery device of claim 1, configured to deliver a drug comprising pegfilgrastim.

19. The on-body drug delivery device of claim 6, wherein said cut-outs and perforations are spaced from the peripheral edge of said substrate and contained within said perimeter.

* * * * *